(12) United States Patent
Conio et al.

(10) Patent No.: US 9,398,983 B2
(45) Date of Patent: *Jul. 26, 2016

(54) MATRIX-CONSTRUCTION PADDED ABSORBING ARTICLE AND MAKING METHOD THEREFOR

(75) Inventors: Guido Conio, Lacchiarella (IT); Giorgio Mantovani, Lacchiarella (IT)

(73) Assignee: CORMAN S.P.A., Lacchiarella (MI) (IT)

( * ) Notice: Subject to any disclaimer, the term of this patent is extended or adjusted under 35 U.S.C. 154(b) by 404 days.

This patent is subject to a terminal disclaimer.

(21) Appl. No.: 12/927,333

(22) Filed: Nov. 12, 2010

(65) Prior Publication Data

US 2011/0118688 A1    May 19, 2011

(30) Foreign Application Priority Data

Nov. 13, 2009   (IT) .............................. MI2009A1998

(51) Int. Cl.
*A61F 13/15*    (2006.01)
*A61F 13/53*    (2006.01)

(52) U.S. Cl.
CPC ........... *A61F 13/15626* (2013.01); *A61F 13/53* (2013.01)

(58) Field of Classification Search
CPC . A61F 13/53; A61F 13/15626; A61F 13/538; A61F 13/5383; A61F 13/5386
USPC ......................................... 604/372, 358, 367
See application file for complete search history.

(56) References Cited

U.S. PATENT DOCUMENTS

| | | | | |
|---|---|---|---|---|
| 3,825,381 | A * | 7/1974 | Dunning et al. | 425/81.1 |
| 4,610,678 | A * | 9/1986 | Weisman et al. | 604/368 |
| 4,636,209 | A * | 1/1987 | Lassen | 604/378 |
| 4,673,402 | A * | 6/1987 | Weisman et al. | 604/368 |
| 4,902,559 | A * | 2/1990 | Eschwey et al. | 442/334 |
| 5,030,229 | A * | 7/1991 | Yang | 604/385.05 |
| 5,047,023 | A * | 9/1991 | Berg | 604/368 |
| 5,681,300 | A * | 10/1997 | Ahr et al. | 604/367 |
| 6,037,518 | A * | 3/2000 | Guidotti et al. | 604/378 |
| 6,231,557 | B1 * | 5/2001 | Krautkramer et al. | 604/385.16 |
| 6,455,114 | B1 * | 9/2002 | Goldhirsch et al. | 428/34.7 |
| 6,890,622 | B2 * | 5/2005 | Adam et al. | 428/171 |
| 7,429,689 | B2 * | 9/2008 | Chen et al. | 604/378 |
| 7,759,540 | B2 * | 7/2010 | Litvay et al. | 604/379 |
| 8,357,445 | B2 * | 1/2013 | Hammons et al. | 428/88 |
| 2003/0116888 | A1 * | 6/2003 | Rymer et al. | 264/460 |
| 2003/0118814 | A1 * | 6/2003 | Workman et al. | 428/365 |
| 2005/0049565 | A1 * | 3/2005 | Joseph et al. | 604/367 |
| 2007/0272481 | A1 * | 11/2007 | Birch et al. | 181/284 |

* cited by examiner

*Primary Examiner* — Bradley Philips
(74) *Attorney, Agent, or Firm* — Hedman & Costigan, P.C.; James V. Costigan; Kathleen A. Costigan

(57) ABSTRACT

An absorbing article with a pad having a matrix construction comprises a water impermeable first main sheet, a substantially water permeable second sheet and an absorbing pad member arranged between the first and second sheets, the absorbing pad member having an absorbing layer including a flexible matrix made of cotton fibers and superabsorbing polymer fibers, the cotton fibers of the pad matrix having a random three-axis orientation and do not have a preferred X-Y orientation.

3 Claims, 2 Drawing Sheets

MATRIX-CONSTRUCTION PADDED ABSORBING ARTICLE AND MAKING METHOD THEREFOR

BACKGROUND OF THE INVENTION

The present invention relates to matrix-construction padded absorbing article and a method for making said padded absorbing article.

More specifically, the present invention relates to an absorbing construction to be used in disposable sanitary products which are preferably, though not exclusively, used by incontinent women.

As is known, "SAP" is a polymeric material suitable to absorb a comparatively large amount of fluids and to restrain the absorbed fluid under a low pressure.

The above features make said polymeric material suitable for making absorbing structure for incontinence products.

The absorbance efficiency of such a SAP material, in disposable absorbing articles, depends in a high degree on the material shape, position and the manner by which SAP is embedded in the article.

In some cases, in particular as the SAP density is a high one, his efficiency may be negatively affected by the so-called "gel-blocking" phenomenon.

This term is indicative of a situation occurring as the SAP material is in a wet swollen condition, thereby preventing the liquid from arriving at the absorbing article inner parts.

In actual practice the absorbing article absorb the intended fluid with an absorbing rate less than the human body releasing rate, thereby causing excess fluid losses; and this a long time before a full saturation of the SAP material in the article is achieved.

As the SAP material density increases, correspondingly increases the gel-blocking phenomenon.

On the other hand, a high SAP concentration would be desirable to achieve a sufficient article absorbing capability.

Several approaches have been devised to improve the SAP efficiency in absorbing articles, to reduce the above disclosed gel-blocking phenomenon.

Thus, it would be possible to improve the SAP efficiency by causing SAP to assume a spherical configuration in a wet condition.

To hold a typically spherical configuration means to leave inner interstitial free spaces for allowing fluid to enter them.

In addition to the absorbing capability, in particular in a slight incontinence article, the fluid absorption rate is another very important parameter to provide the article with an optimum performance.

In fact, in a typical slight/average incontinence person, the urine flow is characterized by a small amount and high flow rates, since the urine release is related to a temporary control loss by the incontinent person, typically in sneezing, laughing or abrupt effort events.

Thus, in incontinence products, the instantaneous urine acquirement or absorbing rate is much more important than the overall article absorbing capability.

However, an increase of the article absorbing capability, though it would be very desirable, would not be sufficient to assure per se a good operating performance.

For increasing the incontinence article absorbing rate without undesirably reducing the superabsorbing polymer material amount thereof, it is possible to use multiple layer constructions or structures in which the absorbing core parts comprise cellulose fibers with the superabsorbing polymer embedded therein.

To allow the article to operate to transport liquids by a capillarity phenomenon, in which the cellulose fibers would operate as a vehicle for conveying urine to the superabsorbing polymeric material.

However, in actual practice, the above mentioned gel-blocking phenomenon would hinder a proper liquid or liquid diffusion through the article by capillarity.

To overcome such a limitation, it would be also possible to use a so-called distributing or acquirement layer, in addition to the absorbing pad layer proper.

Generally, such an acquirement layer comprises specially processed cellulosic or non woven material fibers, and a comparatively small amount of superabsorbing polymer.

Multiple layer constructions including different superabsorbing polymers in each layer thereof, have also been designed and made.

FIG. 1 shows a prior absorbing pad construction, including a liquid receiving layer 1, not including a superabsorbing polymer, designed for quickly receiving and distributing urine, and an underlying layer 2, constituting the pad proper, with the superabsorbing polymer arranged therein.

As shown, said underlying layer 2 is arranged between two sheet elements, that is a first sheet element 3 permeable to liquids and contacting the user body, and a second sheet element which is a person garment facing impermeable sheet 4.

Such a prior construction comprises moreover a first layer having an urine acquirement but not absorbing function, and consequently undesirably remaining wet and contacting the user skin, which may cause user skin irritating and sensitizing phenomena.

On the contrary, a properly operating absorbing article, should preserve an integral and fully operating condition even if it is in a wet status, which characteristic could be achieved both by binding (by chemical or mechanical methods) the absorbing layer forming fibers, and using fibers having such an average length as to provide, in a interbraided arrangement, a stiff network structure.

However, in actual practice, the above methods excessively stiffen the absorbing pad, thereby undesirably reducing the article softness and comfort properties.

A cotton material has very long fibers and, accordingly, would be ideally suitable to form interbraided and strong absorbing constructions; however a cotton material is not at present used in absorbing articles, since it is much, more expensive than wood cellulose fibers, and cannot be easily processed into absorbing articles, since prior cotton material absorbing articles are conventionally made by overlapping onto one another a plurality of textile fiber web layers deriving from carding processes or formed by blowing or pressing methods in which are used a plurality of cascade arranged carding machines to comb the cotton fibers and form a continuous mattress to be subjected to further cutting and shaping processes.

Moreover, a main limitation of these prior methods is that the absorbing articles made thereby comprise fibers which are oriented in the longitudinal direction of the article and preferably conveying the liquid through a X-Y plane and not in the depth direction of the article.

Another drawback is that of the so-called "hourglass shape" caused by mechanical cutting operations, which undesirably make the pad contour stiffener with objectable aesthetic and a functional characteristics, since said cutting operation cause reddening phenomena at the article user skin contacting points.

Moreover, the constant thickness and basis weight through the overall length of such a prior absorbing article prevent the absorbing material amount and absorbing capability from being properly selected and increased.

SUMMARY OF THE INVENTION

Accordingly, the aim of the present invention is that of providing a method for making an absorbing article overcoming the above prior art drawbacks.

Within the scope of the above mentioned aim, a main object of the invention is to provide such an absorbing article, in particular a slight incontinence absorbing article, which is ideally suitable to quickly absorb and properly control high urine flows.

Another object of the present invention is to provide such an absorbing article, which has such an absorbing capability as to collect high urine multiple loads.

Another object of the present invention is to provide such a slight incontinence absorbing article which is adapted to hold an integral condition notwithstanding repeated mechanical stresses it is subjected to due to the user leg movements and repeated urine absorbing events.

Another object of the present invention is to provide such a slight incontinence absorbing article preventing the user skin from being reddened or irritated.

Yet another object of the present invention is to provide such an absorbing article having an absorbing article structure with an improved liquid acquiring speed or rate and an overall article high absorbing capability.

According to one aspect of the present invention, the above mentioned aim and objects, as well as yet other objects, which will become more apparent hereinafter, are achieved by an absorbing article with a pad having a matrix construction and a method for making it, said absorbing article comprising a water permeable first main sheet, a substantially water impermeable second sheet and an absorbing pad arranged between said first and second sheets.

Said absorbing pad being characterized by an absorbing layer including a flexible matrix made of cotton fibers and superabsorbing polymer fibers, said cotton fibers of said pad matrix having a random three-axis orientation without any X-Y plane preferred orientation.

In particular, the above cotton fiber matrix construction is achieved by a novel process step sequence, constituting the making method according to the present invention.

The above processing sequence comprises a cotton fiber opening and separating process, for separating the cotton fibers by a properly conveyed air flow and a fiber collection process to collect the cotton fibers in a form member having a target configuration and size.

Said form member is mounted on a rotary drum and is filled-in by a revolution rotary movement, in a constant manner, to allow the system to operate according to a continuous operating process.

The method according to the present invention provides to orient the cotton fibers also in the Z axis direction and not only in the X-Y direction.

This allows the fluid or urine material to be also conveyed to the innermost layers of the article, while distributing said fluid on all the free Cartesian axes and reducing the gel-blocking phenomenon.

BRIEF DESCRIPTION OF THE DRAWINGS

Further characteristics and advantages of the present invention will become more apparent hereinafter from the following detailed disclosure of a preferred, though not exclusive, embodiment of the invention, which is illustrated, by way of an indicative, but not limitative, example in the accompanying drawings, where.

DESCRIPTION OF THE PREFERRED EMBODIMENTS

Figure 1:
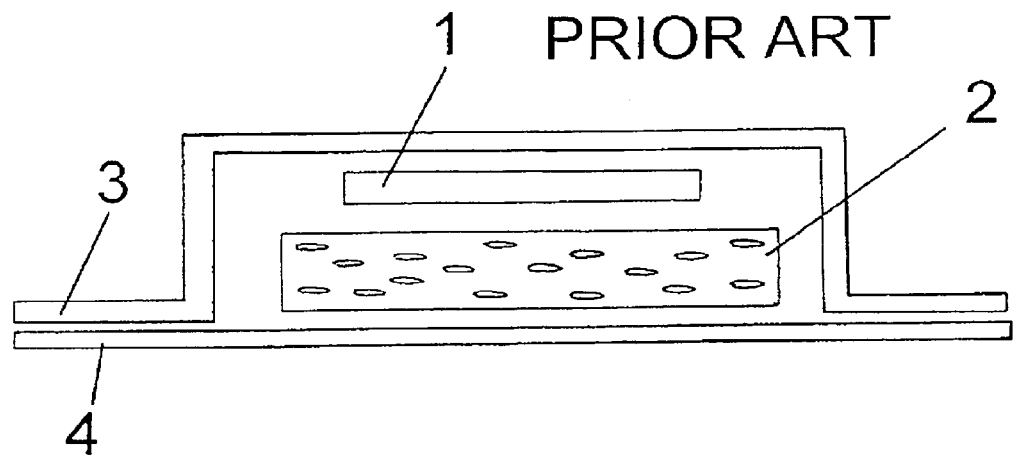
FIG. 1 is a cross-sectional view of a prior absorbing article.
Figure 2:
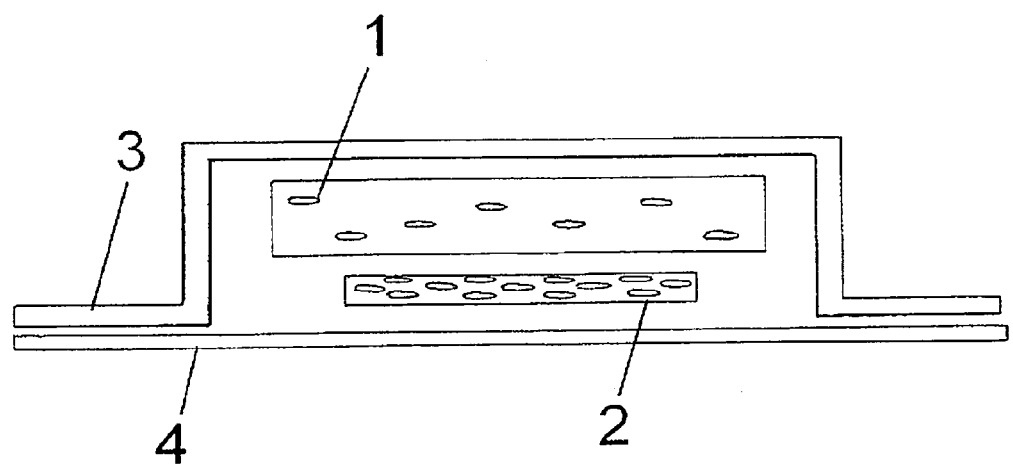
FIG. 2 is a further cross-sectional view of a preferred embodiment of the absorbing article pad according to the present invention.

With reference to the number references of the above mentioned figures, the absorbing article according to the present invention, comprises an absorbing pad including a first top cotton and superabsorbing polymeric material particle matrix layer 1, and a second bottom layer 2 including cellulosic fibers and the superabsorbing polymeric material particles.

The absorbing pad is arranged on a bottom water impermeable or substantially impermeable sheet element, indicated generally by the reference number 4, and conventionally called "backsheet", and, above said pad a water permeable or substantially permeable top sheet 3, conventionally called "topsheet", is arranged.

Hereinbelow the terms used in this disclosure and the meanings attributed thereto will be briefly discussed.

The term "Z dimension" or "Z-axis" is related to a dimension orthogonal to a plane defined by the article length and width. The Z axis usually corresponds to the layer construction or article thickness;

The term "X-Y sides" or "X-Y plane" is related to the plane defined by the article length and width;

The term "nonwovens" or "non woven fabric" is related to a cloth or fabric article having a construction including a plurality of interbraided or intertwined individual fibers, either with a repeating pattern or a non repeating pattern, in which a non-woven product may be made by a plurality of non-woven product making methods, such as meltblowing, spunbonding and carding processes;

The term "particle" or "grain-granule" is related to a material comprising a plurality of very small discrete units, such as powders, balls and particle materials.

The preferred shape of such a grain or granule comprises, for example, a cubic, cylindric, polyhedric, spherical, semi-spherical, uneven configuration or a combination thereof.

Such a definition will obviously comprise any granule shapes having a dimension much larger than the others, such as a needle, thread and fiber.

Moreover, the preferred particle may be coated by a coating gel, film, protein or the like and may further comprise a core part or particle.

Alternately, the particle may be a non-coated one.

Moreover, the term "particle" may also be related to an agglomerated configuration, comprising several granules, particles or the like;

The term "superabsorbing material" or "SAP" or "polymer" is related to an absorbing material designed for absorbing and holding therein at least 10 grams of an aqueous liquid, such as water, a saline solution or a synthetic urine solution, such as the product K-C 399105 by the PPG Company, for each gram of absorbing material as the latter is held immersed in a liquid for hours and being then subjected to a 0.5 psi pressure;

The term "cotton" or "cotton fibers", is related to fibers made from cotton seeds or a mixture thereof with any other desired fiber materials, provided that the cotton fibers are present in a prevailing amount.

The subject matter of the present invention is a method for making a single-use or disposable absorbing article adapted to absorb large amounts of water and body fluids, such as menstrual fluids, urine, sweats, feces.

Thus, the inventive article may be made as a woman absorbing product, child napkin, incontinence article and the like.

While hereinbelow a preferred embodiment of the inventive article designed for a slight incontinence situation will be disclosed, it should be pointed out that the invention may be easily extended to any other suitable embodiments designed for absorbing body fluids, such as woman absorbing articles, napkins, incontinence products, bed protecting products and the like.

Available sanitary products generally comprise, as it is well known, three basic constructional components.

The first is a impermeable or substantially impermeable sheet, usually called "backsheet". Above this sheet an absorbing component, conventionally comprising two or more layers, is arranged.

Such an absorbing component is usually overall called "the pad".

Above this pad a water permeable or substantially permeable sheet, the so-called "topsheet" is arranged.

The pad according to the present invention comprises at least an absorbing layer formed by a flexible cotton fiber matrix.

Said cotton fibers are much longer than the cellulosic fibers which are conventionally used in prior like articles, and provide a construction matrix which has very good interbraiding, resilient and strength properties in a wet condition.

The matrix base weight may vary from 50 to 1,000 g/square meter (gsm), preferably from 100 to 800 gsm, more preferably from 150 to 600 gsm.

The fibers are arranged with a 3D random arrangement, and no preferred arrangement axis exists.

According to a further aspect of the present invention, the above cotton fiber matrix has a base weight varying along the X-Y plane so as to form a so-called "3D core".

In the preferred embodiment of the invention, the central region of the inventive article has a larger base weight, whereas the article peripheral regions have a less base weight.

This structure will operate so as to concentrate the article absorbing capability to the article region where it is mostly required, while providing an absorbing article having a much more ergonomic configuration.

In other embodiments of the invention, the larger and small base weight regions may be also differently arranged.

In the cotton matrix, and, in particular, in the interstices of the fiber network, superabsorbing particles are moreover arranged or embedded.

The amount of said embedded particles will depend on the cotton fiber amount and may vary from 5% to 70% of the overall weight of the cotton fiber and superabsorbing particle matrix overall weight.

More preferably, said rate may vary from 10% to 50%.

Yet more preferably, said rate may vary from 15% to 40%.

Further preferably, the superabsorbing particles are homogeneously mixed with the cotton fibers and, accordingly, they will be present in a higher amount where the cotton fiber matrix base weight is larger.

In a less preferred embodiment of the invention, the superabsorbing material distribution will be fully independent from the cotton fiber matrix structure.

In yet another embodiment of the invention, the X-Y plane contour or profile of the cotton matrix will be preferably tapering to a central portion thereof thereby defining a so-called "hourglass" configuration, or being tapering at an end portion thereof.

This will provide the absorbing article with an anatomic and easy to be used profile.

The method for making the cotton fiber matrix according to the present invention provides an anatomic configuration article without the need of using further treatment processes after having formed the pad, which would negatively affect the article softness and skin anti-irritating properties.

On the contrary, the above prior processes, usually comprising several additional mechanical cutting processes, will increase the article profile hardness, thereby negatively affecting the article wearing comfort characteristics.

More specifically, the above disclosed embodiments of the inventive articles may be made by suitably oriented and conveyed cotton fibers, which are held in a 3D random orientation, and do not have any X-Y plane preferential orientation, as it occurs in the prior art.

Figure 3:
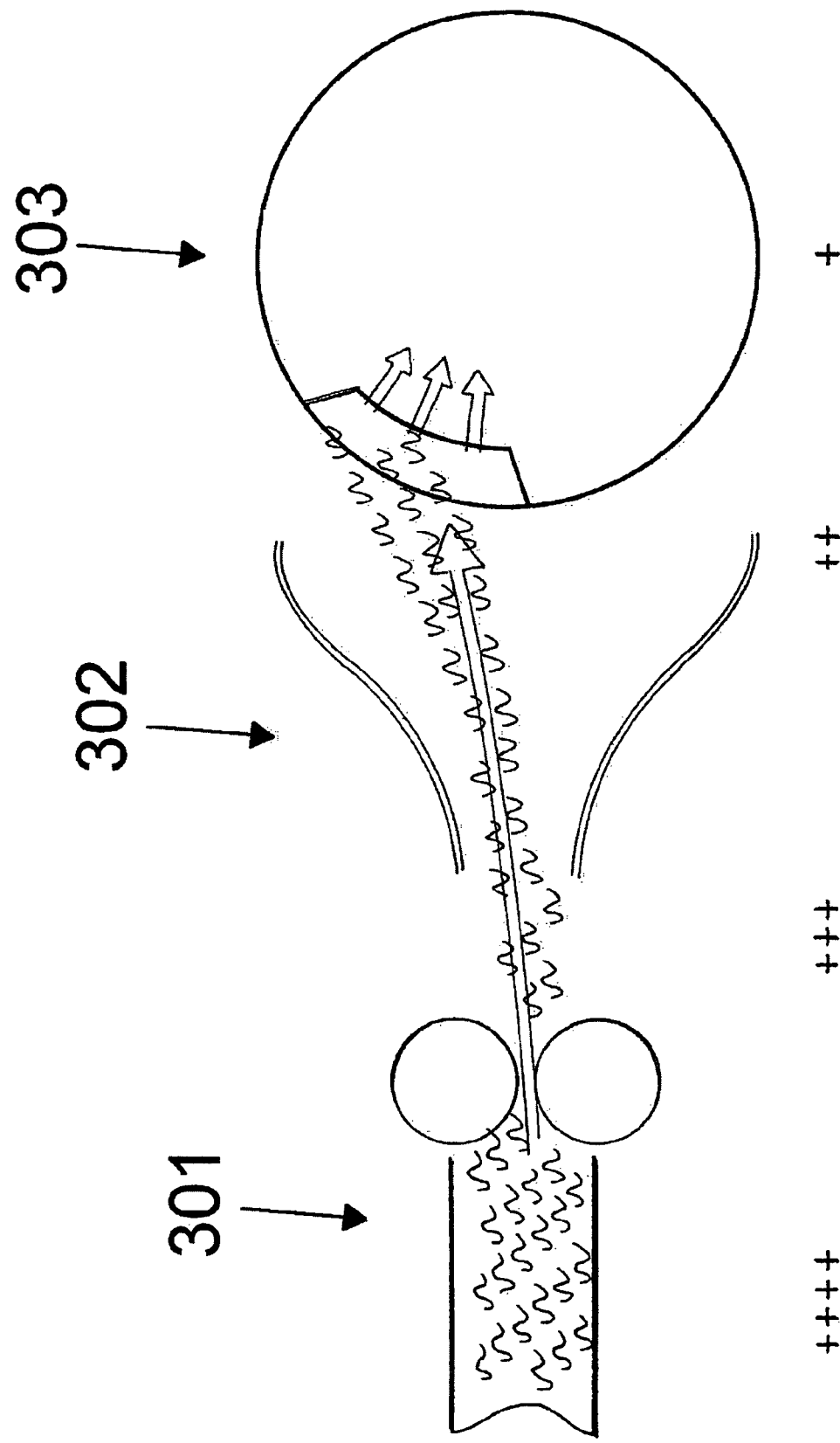
FIG. 3 shows a schematic diagram of a preferred embodiment of a process for making a cotton fiber pad member according to the present invention.

FIG. 3 schematically shows a preferred method for making the inventive pad, in which the reference number 301 indicates a fiber separating region, the reference number 302 a conveying process and the reference number 303 a collecting or merging of the fibers into a form arrangement.

The marks ++++/+++/++/+ of FIG. 3 are used for qualitatively indicating the air pressure level in the process steps.

More specifically, the method according to the present invention comprises at the starting thereof, a cotton fiber opening and separating process, as generally indicated by the reference number 301, for properly separating and orienting the cotton fibers, by rollers including a plurality of rotating and counter-rotating comb member.

The fibers are introduced into an air flow to be conveyed to the following process steps.

The fiber conveying air flow is characterized by a starting higher pressure progressively decreasing to a minimum pressure value achieved at the forming drum 303.

After having being separated and introduced into the air flow, the cotton fibers are conveyed by a conveyor 302 which, owing to its specifically designed wall configuration and vortex arrangements generated thereby, homogeneously mixes or blends the cotton fibers to arrange them with a full random arrangement, without any preferred arrangement direction.

In this operating step, said fibers may be mixed with the superabsorbing polymer thereby providing an homogeneous mixture.

Then, the fully mixed and randomly oriented fibers are conveyed in a form member mounted on a rotary drum.

Said form member has any desired size and shape as to provide a target configuration pad, without the need of performing further contouring or shaping process steps.

Then. the cotton fiber collecting form is folded n times on the drum perimeter, thereby fully covering it.

During the rotary movement of the drum, said form members will be successively filled-in by a continuous material flow coming from the conveyor.

Accordingly, the inventive process is a continuous type of processing method.

It has been found that the invention fully achieves the intended aim and objects.

In practicing the invention, the used materials, as well as the contingent size and shapes, can be any, according to requirements.

The invention claimed is:

1. An absorbing article having reduced gel-blocking phenomena, said absorbing article comprising a bottom water impermeable first main sheet, a top water permeable second sheet and an absorbing pad arranged between said first and second sheets, wherein said absorbing pad consists of two overlapping layers including a first top absorbing layer including a flexible pad matrix comprising of cotton fibers or a mixture of cotton fibers with any other fiber materials provided that the cotton fibers are present in a prevailing amount and superabsorbing polymer material particles, said cotton fibers having a random three-axis orientation without any X-Y plane preferred orientation, and a second bottom absorbing layer of cellulosic fibers and superabsorbing polymer material particles, said superabsorbing particles being homogeneously mixed with said cotton fibers, wherein said cotton fibers define a cotton fiber network including fiber network interstices where said superabsorbing polymer material particles are embedded, wherein said superabsorbing polymer material particles are embedded particles which are embedded in said cotton fibers and constitute an amount from 15% to 40% by weight of the flexible pad matrix, wherein said flexible pad matrix has a base weight from 150 to 660 gsm, and wherein said superabsorbing polymer particles are made of a superabsorbing polymer each gram of which absorbs and holds therein at least 10 grams of a synthetic urine solution.

2. An absorbing article, according to claim 1, wherein said cotton fiber flexible pad matrix has a base weight varying along the X-Y plane so as to form a 3D core.

3. An absorbing article, according to claim 1, wherein said absorbing article has a central region with a base weight larger than that of peripheral regions of said absorbing article.

* * * * *